United States Patent [19]
Fischer et al.

[11] Patent Number: 5,800,928
[45] Date of Patent: Sep. 1, 1998

[54] BREATHABLE WATERPROOF FILM

[75] Inventors: Laurent Fischer, Serquigny; Michel Degrand; Alain Bouilloux, both of Bernay; Jean-Claude Jammet, Glisolles; Yves Germain, Serquigny, all of France

[73] Assignee: Elf Atochem S.A., Puteaux, France

[21] Appl. No.: 492,263

[22] Filed: Jun. 19, 1995

[30] Foreign Application Priority Data

Jun. 20, 1994 [FR] France .................. 94 07514

[51] Int. Cl.⁶ ............................ B32B 27/00
[52] U.S. Cl. ............................ 428/500; 428/523
[58] Field of Search ...................... 428/500, 523

[56] References Cited

U.S. PATENT DOCUMENTS 5,348,804  9/1994  Vasselin et al. ............ 428/423.1
5,506,024  4/1996  Flesher ..................... 428/85

FOREIGN PATENT DOCUMENTS 0 378 015 A1  7/1990  European Pat. Off. .
0 459 862 A1  12/1991  European Pat. Off. .
0 560 630 A1  9/1993  European Pat. Off. .

*Primary Examiner*—Helen L. Pezzuto
*Attorney, Agent, or Firm*—Pennie & Edmonds LLP

[57] ABSTRACT

The invention relates to a breathing film constituting a mixture including:

(a) at least one thermoplastic elastomer which has polyether blocks;

(b) at least one copolymer including ethylene and at least one alkyl (meth)acrylate.

They can be used in combination with fabrics or with nonwovens.

9 Claims, No Drawings

BREATHABLE WATERPROOF FILM

FIELD OF THE INVENTION

The present invention relates to breathable waterproof films. The breathable waterproof films of the present invention comprise at least one thermoplastic elastomer that has polyether blocks and at least one copolymer of ethylene and an alkyl (meth)acrylate.

BACKGROUND OF THE INVENTION

European Patent Application EP 378 015 describes breathable waterproof films that are made of polyetheresteramides which may be adhesively bonded by heating or with the aid of an adhesive onto fabric, leather, or plastic.

European Patent Application EP 0 560 630 breathable waterproof materials that consist (Example 6) of two coextruded films (1) and (2). To each face of the film thus obtained, a nonwoven is adhesively bonded with the aid of a polyurethane-based adhesive in solution in trichloroethylene. The film (1) is a mixture of polyetheresteramide, of polyamide 6, and of polyethylene grafted with maleic anhydride. The film (2) consists of another polyetheresteramide. A polyamide-based nonwoven is adhesively bonded on the side of the film (1). A polyester nonwoven is adhesively bonded on the side of the film (2).

Example 7 of the same prior art describes the same two-layer material consisting of coextruded films (1) and (2), but a nonwoven made of polyester/polyethylene is adhesively bonded on the side of the film (1) and a nonwoven made of polyester is adhesively bonded on the side of the film (2).

This material is employed for making garments by arranging the polyester/polyethylene nonwoven on the inside of the garment and the polyester nonwoven towards the outside of the garment. The material makes the garment permeable to water vapour and impervious to water and to blood splashed from the outside towards the garment, thus protecting the person wearing the garment.

European Patent Application EP 459 862 describes films that consist of a mixture of polyetheresteramide and of a modified polyolefin chosen from: copolymers of ethylene and of vinyl acetate, optionally maleinized; copolymers of ethylene and of (meth)acrylic acid; copolymers of ethylene, of vinyl acetate, and optionally of alkyl (meth)acrylate; and copolymers of ethylene, of alkyl (meth)acrylate, and optionally of maleic anhydride.

These films may be adhesively bonded onto fabrics and nonwovens.

Example 8-1 shows a film that consists of a mixture of a polyetheresteramide and of a maleinized EVA adhesively bonded onto a textile.

The thickness of the films described in EP 459 862 is from 100 to 500 μm. They are not breathable waterproof films.

The breathable waterproof films of the prior art that are based upon polyetheresteramides have the disadvantage, when they are very permeable, of having a high moisture uptake which results in their swelling and makes them fragile.

Films made of blend of polyetheresteramides and polyamides are not supple enough and adhesively bond with difficulty to nonwovens.

SUMMARY OF THE INVENTION

Breathable waterproof films made of blends of polyetheresteramide and copolyacrylates have now been found which have high permeability while having low moisture uptake. A second advantage of the films of the invention is that they are easy to extrude at high speed and without faults. Moreover, they do not block and their appearance is silky. A third advantage is that they have a high elongation at break. A fourth advantage is that they can be easily used in combination with nonwovens.

DESCRIPTION OF THE PREFERRED EMBODIMENTS

The present invention is therefore a breathable waterproof film that comprises a mixture including:

a) at least one thermoplastic elastomer which has polyether blocks; and b) at least one copolymer including ethylene and at least one alkyl (meth)acrylate.

The thermoplastic elastomer may include polyether units and polyester units; these are, for example, polyether blocks and polyester blocks or units.

These products are known under the name of elastomer polyesters and are thermoplastic.

The polyethers are, for example, polyethylene glycol, polypropylene glycol or polytetramethylene glycol.

The molecular mass $\overline{M}n$ of these polyethers may be between 250 and 6 000.

The flexible segments of the elastomer polyesters are formed by the above polyether units and at least one dicarboxylic acid such as, for example, terephthalic acid.

The rigid segments of the elastomer polyesters include glycol, propanediol or 1,4-butanediol units and dicarboxylic acid units connected by ester functional groups. The dicarboxylic acids may be the same as those above.

The rigid segments may include a number of units resulting from the action of a diol on a diacid.

The flexible segments may include a number of units resulting from the action of the polyether on a diacid. The hard segments and the flexible segments are attached by ester bonds. Such elastomer polyesters are described in Patents EP 402 883 and EP 405 227.

The thermoplastic elastomers containing polyether units can also be ester copolyetherimides. The flexible segments are formed by the reaction of polyetherdiamines with tricarboxylic compounds or carboxylic acid anhydrides containing a carboxylic group, such as, for example, trimellitic anhydride. The polyetherdiamines employed have an average molecular mass of 600 to 12 000. These polyetherdiamines may themselves originate from polyethylene glycol, polypropylene glycol or polytetramethylene glycol.

The polyester blocks forming the hard segments in the ester copolyetherimides result, for example, from the condensation of at least one diol with at least one dicarboxylic acid. The diol may be glycol, propanediol or butanediol. The diacid may be terephthalic acid. Such ester copolyetherimides are described in EP 402 883 and EP 405 227.

The thermoplastic elastomers containing polyether blocks may also be polyetherurethanes. They are formed by the chain sequencing of three base components:

(i) a polyetherdiol such as, for example, a polyethylene glycol, a polypropylene glycol or a polytetramethylene glycol. The molecular mass may be from 500 to 6 000;

(ii) a diisocyanate such as an MDI or a TDI;

(iii) a diol of low mass such as glycol (ethanediol), 1,4-butanediol or 1,4-phenylene bis-β-hydroxyethyl ether as chain lengthener.

The elastomers (a) containing polyether blocks can also be polymers containing polyamide blocks and polyether blocks.

Polymers containing polyamide blocks and polyether blocks result from the copolycondensation of polyamide sequences containing reactive ends with polyether sequences containing reactive ends, such as, among others:

1) Polyamide sequences containing diamine chain ends with polyoxyalkylene sequences containing dicarboxylic chain ends.

2) Polyamide sequences containing dicarboxylic chain ends with polyoxyalkylene sequences containing diamine chain ends, obtained by cyanoethylation and hydrogenation of aliphatic alpha, omega-dihydroxylated polyoxyalkylene sequences called polyetherdiols.

3) Polyamide sequences containing dicarboxylic chain ends with polyether diols, the products obtained being, in this particular case, polyetheresteramides.

The polyamide sequences containing dicarboxylic chain ends originate, for example, from the condensation of alpha, omega-aminocarboxylic acids of lactams or of dicarboxylic acids and diamines in the presence of a dicarboxylic acid chain limiter. The polyamide blocks are advantageously made of polyamide-12.

The number molecular mass $\overline{M}_n$ of the polyamide sequences is between 300 and 15 000 and preferably between 600 and 5 000. The mass $\overline{M}_n$ of the polyether sequences is between 100 and 6 000 and preferably between 200 and 3 000.

The polymers containing polyamide blocks and polyether blocks may also include randomly distributed units. These polymers may be prepared by the simultaneous reaction of the polyether and of the precursors of the polyamide blocks.

For example, it is possible to react polyetherdiol, a lactam (or an alpha,omega-aminoacid) and a chain limiter diacid in the presence of a little water. A polymer is obtained which has essentially polyether blocks, polyamide blocks of very variable length, as well as the different reactants that have reacted randomly, which are distributed statistically along the polymer chain.

These polymers containing polyamide blocks and polyether blocks, whether originating from the copolycondensation of polyamide and polyether sequences prepared beforehand or from a one-stage reaction, exhibit, for example, Shore D hardness values which may be between 20 and 75 and advantageously between 30 and 70, and an intrinsic viscosity between 0.8 and 2.5, measured in meta-cresol at 250° C. with an initial concentration of 0.8 g/100 ml.

Whether the polyether blocks originate from polyethylene glycol, polyoxypropylene glycol or polyoxytetramethylene glycol, they are either employed as they are and copolycondensed with polyamide blocks containing carboxylic ends, or they are aminated in order to be converted into polyetherdiamines and condensed with polyamide blocks containing carboxylic ends. They can also be mixed with polyamide precursors and a chain limiter in order to make polymers containing polyamide blocks and polyether blocks which have statistically distributed units.

Polymers containing polyamide and polyether blocks are described in U.S. Pat. Nos. 4,331,786, 4,115,475, 4,195,015, 4,839,441, 4,864,014, 4,230,838 and 4,332,920.

The polyether may be, for example, a polyethylene glycol (PEG), a polypropylene glycol (PPG) or a polytetramethylene glycol (PTMG). The latter is also called polytetrahydrofuran (PTHF).

Whether the polyether blocks are in the polymer chain containing polyamide blocks and polyether blocks in the form of diols or of diamines, they are simply called PEG blocks or PPG blocks or, again, PTMG blocks.

It would not constitute a departure from the scope of the invention if the polyether blocks contained different units, such as units derived from ethylene glycol (—$OC_2H_4$—), from propylene glycol

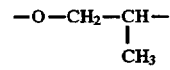

or else from tetramethylene glycol (—O—$(CH_2)_4$—).

The polymer containing polyamide blocks and polyether blocks preferably includes only one type of polyamide block and only one type of polyether blocks. Polymers containing PA-12 blocks and polymers containing PA-6 blocks are advantageously employed.

It is also possible to employ a mixture of two or more polymers containing polyamide blocks and polyether blocks.

The polymer containing polyamide blocks and polyether blocks is advantageously such that the polyamide is the preponderant constituent, that is to say that the quantity of polyamide which is in the form of blocks and that which is optionally distributed statistically in the chain represents 40% by weight or more of the polymer containing polyamide blocks and polyether blocks. The quantity of polyamide and the quantity of polyether are advantageously in the (polyamide/polyether) ratio 1/1 to 3/1 and preferably:

the elastomer (a) may be a mixture of two or more of the elastomers containing polyether blocks referred to above, that is to say that (a) may be a mixture of two polyetherurethanes or of a polyetherurethane and of a polyetheresteramide or any other combination.

The permeability to water vapour varies with the quantity of polyether blocks of (a) and with the nature of these blocks. PEG is very permeable to water vapour.

The alkyl group of the alkyl (meth)acrylate forming part of the copolymer b may have up to 10 carbon atoms and may be linear, branched or cyclic. By way of illustration of the alkyl (meth)acrylate it is possible to mention especially n-butyl acrylate, isobutyl acrylate, 2-ethylhexyl acrylate, cyclohexyl acrylate, methyl methacrylate and ethyl methacrylate. Among these (meth)acrylates preference is given to ethyl acrylate, n-butyl acrylate and methyl methacrylate.

According to a particular form of the invention the copolymer (b) may be grafted or copolymerized with (i) an unsaturated carboxylic acid such as, for example, (meth) acrylic acid, (ii) an unsaturated carboxylic acid anhydride such as, for example, maleic anhydride, or (iii) an unsaturated epoxide such as, for example, glycidyl (meth)acrylate.

(b) may be a mixture of at least two of these copolymers.

According to another form of the invention, (b) is a mixture of a polymer (b1) and of a polymer (b2).

(b2) is a copolymer including ethylene and an alkyl (meth)acrylate. The alkyl (meth)acrylate may be that defined above.

(b1) is different from (b2) and is chosen from:

optionally grafted polyolefin homo- or copolymers such as, for example, polyethylene, polypropylene and the copolymers of ethylene with alpha-olefins, it being possible for these products to be grafted with unsaturated carboxylic acid anhydrides such as maleic anhydride or unsaturated epoxides such as glycidyl methacrylate;

copolymers of ethylene with at least one product chosen from (i) unsaturated carboxylic acids, their salts, their esters, (ii) vinyl esters of saturated carboxylic acids, (iii) unsaturated dicarboxylic acids, their salts, their esters, their monoesters, their anhydrides, (iv) unsaturated epoxides;

it being possible for these ethylene copolymers to be grafted with unsaturated dicarboxylic acid anhydrides or unsaturated epoxides;

styrene/butadiene/styrene (SBS), styrene/isoprene/styrene (SIS) or styrene/ethylene-butene/styrene (SEBS) block copolymers, it being possible for these copolymers to be grafted with an unsaturated carboxylic acid anhydride such as maleic anhydride.

The proportions of (a) and (b) are advantageously such that the mixture is in the form of a matrix of (a) in which (b) is dispersed, for example in the form of nodules. These proportions depend on the nature of (a) and on the nature of (b) and in particular on the acidic, anhydride or epoxy functional groups which may be present in (b).

The quantity of a is advantageously more than 50 parts per 100 parts of (a) and (b), preferably from 55 to 80 parts. (These are parts by weight, and so on in the remainder of the text).

A copolymer containing polyamide blocks connected to polyether blocks is preferably employed as elastomer a, the connection being made via ether bonds (polyetheresteramides).

It can be obtained by condensation of polyamide blocks containing acid ends with polyether blocks containing OH ends.

Polyamides 6 and 12 and polyethylene glycols (PEG) are preferred.

(b1) is advantageously a copolymer including ethylene, at least one alkyl (meth)acrylate and an unsaturated monomer which has an acidic or carboxylic acid anhydride functional group.

The unsaturated monomer of b1, which has an acidic or anhydride functional group may be:

an unsaturated dicarboxylic acid anhydride such as citraconic anhydride, itaconic anhydride, tetrahydrophthalic anhydride, 2-methylmaleic anhydride, 2,3-dimethylmaleic anhydride and maleic anhydride;

an unsaturated acid or diacid such as (meth)acrylic acid, crotonic acid or cinnamic acid.

The copolymer b1 is advantageously an ethylene-alkyl (meth)acrylate-maleic anhydride copolymer containing, by weight, 2 to 10% of maleic anhydride and at least 50% of ethylene.

The alkyl (meth)acrylate of b1 may be chosen from the same class as the (meth)acrylates of b2.

The copolymer b2 advantageously contains 5 to 40% by weight of alkyl (meth)acrylate, and preferably 20 to 35%.

The thermoplastic film of the invention advantageously includes:

a) a polymer containing polyamide blocks and PEG polyether blocks, the polyamide being preferably PA-12;

b) a copolymer of ethylene and of an alkyl (meth)acrylate;

c) an ethylene/alkyl (meth)acrylate/maleic anhydride copolymer.

The preferred proportions are:

60 to 80 parts of a) 20 to 30 parts of b) and 5 to 40 parts of c).

These films have a thickness which may be, for example, between 10 and 80 μm and preferably from 15 to 35 μm.

The polymer mixture which constitutes the breathing impervious film of the invention may optionally contain organic and/or inorganic fillers. Fillers which may be mentioned in particular by way of example are silica and titanium oxide. The mixture may also contain various additives, such as anti-UV agents, demoulding agents impact improvers etc, as well as dyes or pigments.

These mixtures are manufactured by the usual techniques for mixing as a melt, and are then converted into film by techniques which are known per se.

The films of the invention are impervious to water and to aqueous solutions and are permeable to water vapour and are not microporous, that is to say that they are continuous films. They have a good permeability to water vapour, which can reach 25 000 g/m$^2$/24 h according to ASTM standard E 96 BW (films in contact with water).

They have a moisture uptake which is very markedly lower than that of a film consisting essentially of a polymer including PEG blocks.

They can be prepared by high-speed extrusion. The films do not block, are flexible, have a silky feel and are not noisy.

These films can be used for making dressings, patches, ostomy pouches and gloves.

The invention also relates to these objects.

The films of the invention can be bonded onto a textile or on to a nonwoven essentially without adhesive, for example by laminating with heating or by pressing. Adhesives may also be employed either as a complete layer between the breathing waterproof film and the nonwoven or as strips or any noncontinuous application such as points or spots.

These adhesives may be hot melts.

The present invention also relates to these breathing waterproof materials formed by the film of the invention used in combination with a fabric or a nonwoven. It would not constitute a departure from the scope of the invention to add other layers, either on the side of the breathing waterproof film or on the side of the fabric or nonwoven.

These other layers may be fabrics or nonwovens which are identical with or different from those already present.

These breathing waterproof materials made of breathing waterproof film used in combination with a fabric or a nonwoven are flexible and, as the film has a low moisture uptake, it delaminates less easily from the fabric or the nonwoven than does a film consisting only of polymer containing polyether blocks. These materials are useful for making protective garments for medical personnel, disposable hygiene articles, mattress draw sheets, roof-lining films for houses, clothing and footwear.

EXAMPLES

Product (A): namely a polyetheresteramide consisting of block sequences of polyamide 12 $\overline{M}_n=1\ 500$ and of block sequences of polyether glycol (PEG) ($\overline{M}_n=1\ 500$). The intrinsic viscosity, measured at 20° C. in meta-cresol is 1.45 to 1.60.

Product (B): namely a polyetheresteramide consisting of sequences of polyamide 12 ($\overline{M}_n=4\ 500$) and of block sequences of polyether glycol (PEG) ($\overline{M}_n=1\ 500$). The intrinsic viscosity, measured at 20° C. in meta-cresol is 1.4 to 1.55.

Product (C): namely a polyetheresteramide consisting of block sequences of polyamide 6 ($\overline{M}_n=1\ 500$) and of block sequences of polyether glycol (PEG) ($\overline{M}_n=1\ 500$).

Product (D): namely an ethylene-acrylic ester copolymer containing 24% by weight of methyl acrylate.

Product (E): namely an ethylene-acrylic ester copolymer containing 28% by weight of methyl acrylate.

Product (F): namely an ethylene-acrylic ester-maleic anhydride terpolymer containing 19% by weight of comonomer and 3% by weight of maleic anhydride.

The following mixtures are produced on a Buss PR 46/70 11 D and are extruded under standard conditions suitable for 25-μm film products.

|          | Product (A) | Product (B) | Product (C) | Product (D) | Product (E) | Product (F) |
|----------|-------------|-------------|-------------|-------------|-------------|-------------|
| Mixture 1 | 60 |    |    | 30 |    | 10 |
| Mixture 2 |    | 60 |    | 30 |    | 10 |
| Mixture 3 |    |    | 20 |    | 70 | 10 |
| Mixture 4 | 65 |    |    |    |    | 35 |

The water vapour permeability is measured according to the method described in ASTM standard E 96 method BW (film in contact with water) in a Heraous Votsch oven in conditions of temperature=38° C. and ambient relative humidity=50%, maintained throughout the period of the measurement.

The water vapour permeability result is given in g/m$^2$/24 h.

The measurement errors yield a result of plus or minus 10 to 20%.

The moisture uptake of the products is measured using the weight increase of granules which are soaked for 24 h in water at 20° C. and conditioned beforehand in an atmosphere at 20° C. and 65% relative moisture for 15 days.

The extrudability of the products is evaluated by measuring the maximum drawing speed for producing a 25-μm film without having any phenomenon of resonance of the film edges ("necking") on leaving the extruder.

The blocking of the film reeled after extrusion is evaluated qualitatively using the ease of separation of 2 rolled-up films.

The pleasant feel of the film is evaluated manually.

The noisiness of the film when crushed is evaluated; a "good" result being the absence of noise.

The following table is obtained:

| Products or mixtures | Permeability to water vapour g/m$^2$/24 h | Moisture uptake (%) | Extrudability (in m/min) | Film blocking (*) | Feel (*) | Noise (*) |
|---|---|---|---|---|---|---|
| (A) | 23 000 | 50 | ≦50 | – | 0 | 0 |
| (B) | 12 000 | 12 | ≦60 | + | 0 | – |
| (C) | ≧20 000 | 120 |    |    |    | 0 |
| (D) or (E) | ≦350 | ≦2 | ≧100 | + | + | + |
| 1 | 22 000 | 27 | ≧100 | + | + | + |
| 2 | 11 000 | 8 | ≧100 | + | + | + |
| 3 | 300 | 5.5 |    |    |    | + |
| 4 | 22 000 | 27 | ≧100 | 0 | 0 | + |

(*) (+) Good
(0) Average
(−) Bad

The tensile modulus is measured according to ASTM standard D 882 (strip w=15 mm, s=10 mm/min, 1$_o$=100 min) on the films in question in the direction perpendicular to and the direction parallel to the extrusion.

| Product | (A) | 1 | (B) | 2 |
|---|---|---|---|---|
| Direction parallel to the extrusion |  |  |  |  |
| Modulus | 79 MPa | 46 MPa | 235 MPa | 189 MPa |
| Breaking stress | 30 MPa | 29 MPa | 50 MPa | 61 MPa |
| Break elongation | ≧600% | ≧600% | ≧500% | ≧500% |
| Direction perpendicular to the extrusion |  |  |  |  |
| Modulus | 80 MPa | 42 MPa | 230 MPa | 162 MPa |
| Breaking stress | 22 MPa | 23 MPa | 43 MPa | 38 MPa |
| Break elongation | ≧600% | ≧600% | ≧600% | ≧600% |

It is seen that:

Mixture 1

Retention of the permeability to water vapour, compared with (A);

Decrease of nearly a half in moisture uptake, compared with (A);

Increase in the extrudability speed, compared with (A);

Better feel, compared with (A);

Much less blocking, compared with (A);

Better adhesion to PP or PE nonwoven, compared with (A).

Retention of the mechanical properties at break (elongation, stress), but very marked decrease in the modulus of the film. The film is more supple, less noisy and the feel is silky.

Mixture 2

Same as Example 1, compared with (B).

Mixture 3

No improvement in permeability, compared with (E).

Mixture 4

Same as Example 1 with less improvement in the blocking and the feel.

What is claimed is:

1. A breathable waterproof film of a mixture which comprises:
    a) at least one thermoplastic elastomer having polyether blocks; and
    b) at least one copolymer of ethylene and at least one alkyl (meth)acrylate.

2. The film according to claim 1, wherein said polyether blocks are poly(ethylene glycol) blocks.

3. The film according to claim 1, wherein component b) is grafted or copolymerized with (i) an unsaturated carboxylic acid, (ii) an unsaturated carboxylic acid anhydride, or (iii) an unsaturated epoxide.

4. The film according to claim 1, wherein component b) is a mixture of (b1) and (b2) wherein
    (b2) is a copolymer including ethylene and an alkyl (meth)acrylate, and
    (b1) is different from (b2) and is selected from the group consisting of:
    optionally grafted polyolefin homopolymers or copolymers;
    optionally grafted copolymers of ethylene with at least one member selected from the group consisting of (i) unsaturated carboxylic acids, salts, or esters, (ii) vinyl esters of saturated carboxylic acids, (iii) unsaturated dicarboxylic acids, salts, esters, or anhydrides, and (iv) unsaturated epoxides; and
    optionally grafted block copolymers selected from the group consisting of styrene/butadiene/styrene, styrene/isoprene/styrene, and styrene/ethylene/butene/styrene.

5. The film according to claim 4, wherein (b1) is a copolymer that comprises ethylene, at least one alkyl (meth) acrylate, and an unsaturated monomer having an acidic or carboxylic acid anhydride functional group.

6. The film according to claim 1, wherein component a) is a copolymer having polyamide blocks and polyether blocks.

7. A breathable waterproof film of a mixture which comprises:

a major proportion by weight of a thermoplastic elastomer comprising a polyetheresteramide block copolymer; and a minor proportion by weight of an ethylene/alkyl (meth) acrylate copolymer and of an ethylene/alkyl (meth) acrylate/maleic anhydride copolymer.

8. The breathable waterproof film according to claim 7, having a thickness of from about 10 through about 80 micrometers.

9. The film according to claim 1 wherein the alkyl (meth)acrylate is selected from the group consisting of n-butyl acrylate, isobutyl acrylate, 2-ethylhexyl acrylate, cyclohexyl acrylate, methyl methacrylate, and ethyl methacrylate.

* * * * *